United States Patent
Kern et al.

(10) Patent No.: US 9,933,340 B2
(45) Date of Patent: Apr. 3, 2018

(54) METHOD FOR PERFORMING IMMUNOASSAYS UNDER WEIGHTLESSNESS

(71) Applicants: Peter Kern, Salem (DE); Herbert Backes, Saarbruecken (DE)

(72) Inventors: Peter Kern, Salem (DE); Herbert Backes, Saarbruecken (DE)

(73) Assignee: Airbus DS GmbH, Taufkirchen (DE)

( * ) Notice: Subject to any disclaimer, the term of this patent is extended or adjusted under 35 U.S.C. 154(b) by 374 days.

(21) Appl. No.: 14/377,188

(22) PCT Filed: Feb. 15, 2013

(86) PCT No.: PCT/EP2013/053072
§ 371 (c)(1),
(2) Date: Aug. 7, 2014

(87) PCT Pub. No.: WO2013/131733
PCT Pub. Date: Sep. 12, 2013

(65) Prior Publication Data
US 2015/0011011 A1     Jan. 8, 2015

(30) Foreign Application Priority Data

Mar. 3, 2012  (EP) .................................. 12001451

(51) Int. Cl.
*G01N 1/28* (2006.01)
*G01N 33/543* (2006.01)

(52) U.S. Cl.
CPC ......... *G01N 1/28* (2013.01); *G01N 33/54333* (2013.01); *B01L 2200/10* (2013.01); *G01N 2446/10* (2013.01); *Y10T 436/25* (2015.01)

(58) Field of Classification Search
CPC ........................................................ G01N 1/28
USPC ........................................................ 436/174
See application file for complete search history.

(56) References Cited

U.S. PATENT DOCUMENTS

| 5,173,262 A | * | 12/1992 | Burtis ............... B01L 3/502753 |
| | | | 422/50 |
| 5,206,159 A | | 4/1993 | Cohen et al. |
| 5,627,041 A | * | 5/1997 | Shartle .................. B01F 5/0604 |
| | | | 422/50 |

(Continued)

FOREIGN PATENT DOCUMENTS

| CN | 1580763 A | 2/2005 |
| CN | 101545902 A | 9/2009 |

(Continued)

OTHER PUBLICATIONS

Office Action dated Jun. 30, 2015 issued in corresponding CN patent application No. 201380012324.0 (and English translation).

(Continued)

*Primary Examiner* — Christine T Mui
*Assistant Examiner* — Emily R. Berkeley
(74) *Attorney, Agent, or Firm* — Posz Law Group, PLC

(57) ABSTRACT

A method for controlled movement of magnetic carriers in a sample volume for performing immunoassays under weightless or reduced-weight conditions, wherein the magnetic carriers are moved inside the sample volume by means of permanent magnets movably arranged relative to at least one spatial axis of the sample volume.

9 Claims, 3 Drawing Sheets

(56) References Cited

U.S. PATENT DOCUMENTS

Figure 1:
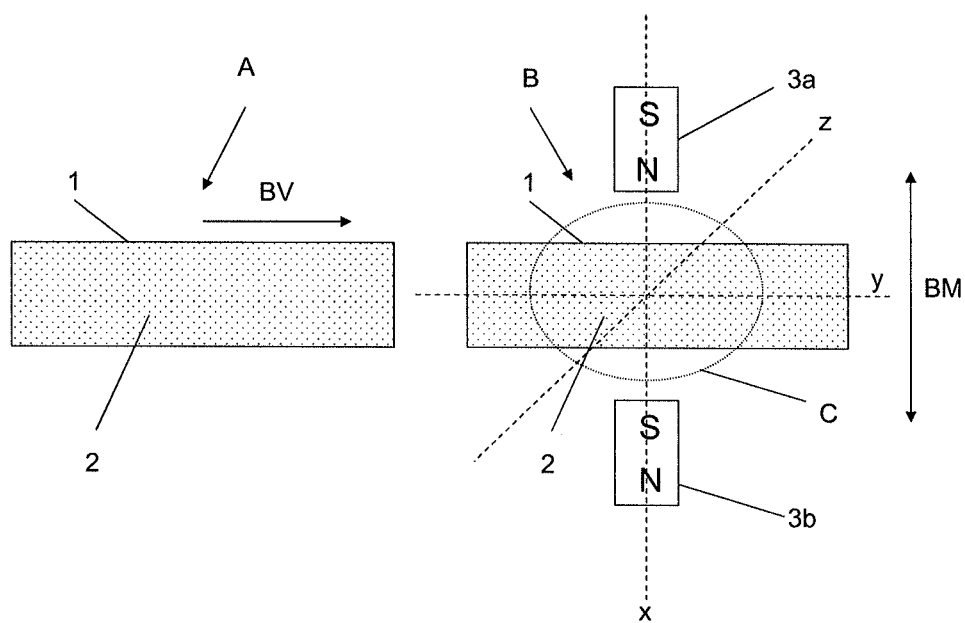

| | | | |
|---|---|---|---|
| 6,043,068 A * | 3/2000 | Maekawa | C02F 3/108 252/62.54 |
| 6,884,357 B2 | 4/2005 | Siddiqi | |
| 2005/0013741 A1 * | 1/2005 | a'Brassard | B03C 1/288 210/695 |
| 2005/0202573 A1 * | 9/2005 | Koyata | G01N 33/553 436/526 |
| 2006/0286563 A1 * | 12/2006 | Lin | G01N 33/54373 435/6.19 |
| 2011/0262895 A1 | 10/2011 | Harding et al. | |

FOREIGN PATENT DOCUMENTS

| | | |
|---|---|---|
| JP | 2010-512531 A | 4/2010 |
| JP | 2010-230683 A | 10/2010 |

OTHER PUBLICATIONS

European Search Report dated Aug. 8, 2012 issued in corresponding EP patent application No. 12001451.9 (and partial English translation).

International Search Report and Written Opinion of the International Searching Authority dated May 8, 2013 issued in corresponding International patent application No. PCT/EP2013/053072 (and English translation).

Moser, Y. et al. "Active superparamagnetic bead manipulation for immunoassays on-chip" Tewntieth International Conference on Minaturized Systems for Chemistry and Life Sciences. Oct. 12, 2008. pp. 1372-1374 (cited in the European and PCT Search Reports).

Rida, A. et al. "Manipulation of Self-Assembled Structures of Magnetic Beads for Microfluidic Mixing and Assaying" Analytical Chemistry, American Chemical Society, vol. 76, No. 21, Nov. 1, 2004. pp. 6239-6246 (cited in the European and PCT Search Reports).

Youngeun, Kwon et al. "Magnetic Bead Based Immunoassay for Autonomous Detection of Toxins" Analytical Chemistry, American Chemical Society, vol. 80, No. 22, Nov. 15, 2008. pp. 8416-8423 (cited in the European and PCT Search Reports).

Office Action dated Oct. 25, 2016 issued in corresponding JP patent application No. 2014-559146 (and English translation).

Office Action dated Mar. 17, 2017 issued in corresponding CA patent application No. 2,866,087.

\* cited by examiner

METHOD FOR PERFORMING IMMUNOASSAYS UNDER WEIGHTLESSNESS

CROSS REFERENCE TO RELATED APPLICATIONS

This application is a U.S. national stage application of PCT/EP2013/053072 filed on Feb. 15, 2013, and claims priority to, and incorporates by reference, European Patent Application No. 12001451.9 filed on Mar. 3, 2012.

The invention relates to a method for moving magnetic carriers in a controlled manner in a sample volume for performing immunoassays according to the present disclosure.

In biochemical analysis, the use of immunoassays is widespread. This method allows selective quantitative or qualitative determination of single (monoplex) or several (multiplex) analytical parameters in a mostly complex biological matrix, such as for example blood, plasma, serum, urine, saliva, tears, sweat, culture media, cell extracts, cell suspensions, etc., which can contain a large number of substances.

The general principle of immunoassays is that the desired analyte selectively binds to a specific protein-based capture antibody or to specific DNA, RNA or functional subgroups or segments based thereon (capture antibody=cAB) and is labeled by a detection antibody (detection antibody=dAB). The cAB is mostly situated on a stationary carrier (solid phase).

In the standard literature, the nomenclature of the term "immunoassay" is inconsistent. Below, both for classical immunoassays, and also ELISA (ELISA=enzyme linked immunosorbent assay) with the use of enzymes, the term "immunoassay" is understood to mean that:
a) in classical immunoassays, the dAB carries either a dye or a fluorophor, which are detected by spectrometry or fluorimetry.
b) the ELISAs (ELISA=enzyme linked immunosorbent assay) are a further immunoassay modification. These use an enzyme bound to dAB as the functional label element. Since the start of the 1980s, the ELISAs have replaced the RIAs (Radio-Immuno Assays) which used a radioisotope as the label. The enzyme bound to the analyte-antibody complex via the dAB converts an added enzyme-specific substrate into a detectable substance which can be detected in the solution by spectrometry or fluorimetry or by means of another physical effect, e.g. chemiluminescence.

In terrestrial use, the various solutions/substance are added sequentially. The free, non-bound substances/reactants are removed by washing steps. The complexes formed remain because of their binding to the stationary phase in the reaction vessel, where they can then be detected.

Mobile carriers are a special form of the solid phase. These are so-called beads (diameter: nm-mm, but mostly a few μm), onto the surface whereof the cAB molecules are bound. After the washing step, these carriers are separated from the supernatant or the residual solution by centrifugation or in the case of magnetic carriers by means of strong magnets. After completion of the overall reaction of the immunoassay, in terrestrial applications the labeled carriers are read off either in a flow cytometer, a reading device for multiwell plates or an array reader. This can be effected as an integral measurement value or by image processing for each individual carrier or each array spot.

The steps described apply for immunoassays as a sandwich assay, as a competitive assay or also in the form of an ELISA.

Immunoassays are also to be used in space flights under reduced gravity, or even weightlessness (μg). This means that substance transport or substance separation are slowed or entirely prevented because of the reduced or absent gravity. During sample preparation on Earth, the reaction partners are moved in special mechanical mixers (e.g. orbital mixers or orbital shakers). Sedimentation for the observation occurs by means of gravity.

Immunoassays with magnetic carriers are widespread for use on Earth below 1 μg. Previously, however, the magnetic carriers were primarily used for separation during a washing step. The terrestrial procedures for immunoassays, for cell concentration or separation are not suitable for use in space.

The objective of the invention is to provide a process with which the implementation of immunoassays with magnetic carriers is possible under weightlessness or reduced gravity.

This problem is solved by the method according to the present disclosure and the advantageous embodiments therein.

According to the invention, for moving magnetic carriers in a controlled manner in a sample volume for performing immunoassays under weightlessness, the magnetic carriers within the sample volume are moved by means of permanent magnets slidably arranged relative to at least one spatial axis of the sample volume and for mixing of the magnetic carriers the permanent magnets arranged on one spatial axis are moved in phase.

The use of magnetic carriers e.g. as a solid phase enables active, controlled, convective mixing of the reaction partners by external magnetic fields which for example operate sequentially from different directions. In addition, the substance transport is improved and the reaction rate increased. A further advantage is that the procedure becomes reproducible under weightlessness.

Finally, planar positioning of the magnetic particles for the purpose of detection (e.g. in the focal point of a microscope) is possible through a directed magnetic field which can be deliberately activated at a predetermined time.

Furthermore, it is possible to collect or hold the magnetic carriers in a defined region, e.g. during a change of fluid or a washing process, by means of a directed magnetic field which can be deliberately activated.

In addition, the magnetic carriers which are coated with a cAB can also be used for binding to specific cell types or membrane receptors, and in space experiments with reduced gravity these can be separated or concentrated or supplied by mechanical displacement for detection.

The absent or reduced gravity during the use of immunoassays in space is compensated by the appropriate use of magnetic carriers. The magnetic carriers are influenced by external magnetic fields activated in a controlled manner depending on the process step.

For mixing of magnetic carriers in a sample volume, the permanent magnets are advantageously arranged diametrically opposite relative to the sample volume.

For positioning of magnetic carriers on one plane within the sample volume, permanent magnets on a spatial axis that is perpendicular to the plane, where the permanent magnets lie, relative to the plane, diametrically opposite the magnetic carriers to be positioned, are advantageously in a first step moved in the direction of the sample volume and in a second step moved away from the sample volume.

Figure 2:
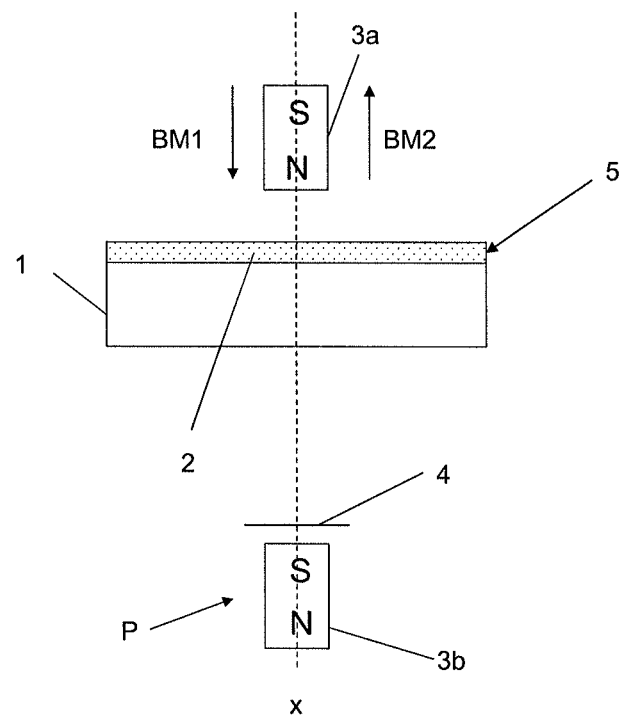
Figure 3:
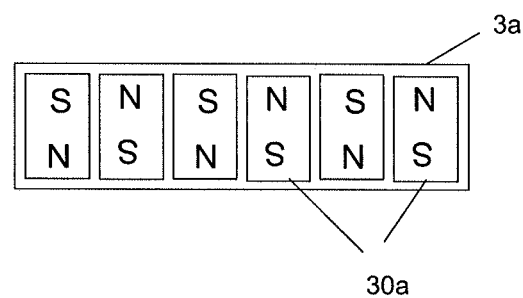

The invention and further advantageous embodiments of the invention are explained in more detail below on the basis of diagrams:

FIG. 1 shows an example of a schematic arrangement for performing the method according to the invention in a first application, FIG. 2 shows an example of a schematic arrangement for performing the method according to the invention in a second application, and FIG. 3 shows an example of an implementation of a permanent magnet.

FIG. 1 shows an example of a schematic arrangement for mixing magnetic carriers 2 within a sample volume 1. Outside the sample volume 1, permanent magnets 3a and 3b are arranged on one spatial axis x,y,z of the sample volume 1. For clearer representation, only 2 permanent magnets 3 on the spatial axis x are shown in FIG. 1. Of course, further permanent magnets 3a and 3b can be arranged on the other spatial axes y and z.

The two permanent magnets 3a and 3b are arranged diametrically opposite relative to the sample volume 1, i.e. the sample volume 1 can be introduced into a region C between the two permanent magnets 3a and 3b. As is well-known, each permanent magnet 3a and 3b consists of a north pole N and a south pole S. It is advisable that the two permanent magnet 3a and 3b are arranged so that in each case the north and south pole are facing.

FIG. 1 shows the arrangement with the sample volume 1 in a first position A, in which the sample volume 1 is situated outside the region B between the two permanent magnets 3a and 3b. The sample volume 1 can be shifted according to the arrow direction BV into a position B, so that the sample volume 1 is situated in the region C. Of course, it is also possible that the two permanent magnets 3a and 3b are appropriately shifted.

For mixing of the magnetic carriers 2 in the sample volume 1, the sample volume 1 is brought into position B. Next, the two permanent magnets 3a and 3b are moved backwards and forwards in phase according to the arrow direction BM. The magnetic carriers 2 are now alternatingly oriented in the sample volume 1 in accordance with the adjacent magnetic field and correspondingly moved. Through the in-phase backward and forward movement of the two permanent magnets 3a and 3b, thorough mixing of the magnetic carriers 2 in the sample volume 1 is effected.

By appropriate arrangement and movement of other permanent magnets on the spatial axes y and z, the mixing can be improved.

FIG. 2 shows an example of a schematic arrangement for positioning magnetic carriers 2 within a sample volume 1. The diagram shows a sample in position B corresponding to FIG. 1. For positioning of magnetic carriers 2 on the plane 5, the permanent magnet 3a, described below as the positioning permanent magnet, which is arranged on an axis x that is perpendicular to the positioning plane 5, is used. This permanent magnet 3a which relative to the positioning plane lies diametrically opposite the magnetic carriers 2 to be positioned can be shifted in accordance with the arrow directions BM1, BM2.

Another permanent magnet 3b relative to the sample volume 1 arranged diametrically to the positioning permanent magnet 3a on the spatial axis x is shifted into a parking position P and protected by means of a screening device 4, so that magnetic fields of the permanent magnet 3b can have no influence on the magnetic carriers 2 in the sample volume 1.

For positioning the magnetic carriers 2 in the sample volume 1, the positioning permanent magnet 3a is shifted in the direction BM1 of the plane 5. Thereby, the magnetic carriers 2 are oriented and moved in the direction of the plane 5. Next, the positioning permanent magnet 3a is shifted in the direction BM2 and shifted into a corresponding parking position P (not shown).

During use in space, the magnetic carriers remain in this position until the end of the detection, since because of the reduced gravity no sedimentation or thermal convection occurs in the sample volume.

FIG. 3 shows by way of example the implementation of a permanent magnet. The permanent magnets are advantageously implemented as a matrix. The permanent magnet 3a comprises several permanent magnets 30a, which are advantageously arranged as a matrix wherein the permanent magnets 30a are arranged alternately.

The invention claimed is:

1. A method for moving magnetic carriers in a controlled manner in a sample volume for performing immunoassays under weightlessness, comprising:
    providing the sample volume in a vessel for performing immunoassays under weightlessness in which no sedimentation and no convective heat transfer occurs in the sample volume due to the weightlessness;
    the magnetic carriers are moved within the sample volume by permanent magnets slidably arranged relative to at least one spatial axis of the sample volume;
    the permanent magnets arranged on one spatial axis are moved synchronized in phase to mix the magnetic carriers; and
    the permanent magnets are shifted into a parking position and protected by a screening device when not used in a process step, wherein
    the permanent magnets comprise several permanent magnets that are arranged as a matrix in which poles of the permanent magnets are arranged alternately, and
    for positioning of magnetic carriers on a plane within the sample volume, the permanent magnets are moved on a spatial axis that is perpendicular to the plane, wherein the permanent magnets lie, relative to the plane, diametrically opposite the magnetic carriers to be positioned, are in a first step moved in the direction of the sample volume and in a second step moved away from the sample volume.

2. The method as claimed in claim 1, wherein the permanent magnets are arranged diametrically opposite relative to the sample volume.

3. The method as claimed in claim 1, wherein
    the permanent magnets are each arranged in the form of an array.

4. The method as claimed in claim 2, wherein
    the permanent magnets are each arranged in the form of an array.

5. The method as claimed in claim 1, wherein
    the sample volume is situated outside the region between the permanent magnets and can be shifted into a region between the permanent magnets.

6. The method as claimed in claim 1, wherein
    the magnetic carriers are solid phase beads of one of the immunoassays.

7. The method as claimed in claim 1, wherein
    the magnetic carriers are a solid phase of one of the immunoassays, and the solid phase is moved via the permanent magnets in order to mix the sample volume in one of the immunoassays.

8. The method as claimed in claim 1, further comprising moving other permanent magnets arranged on at least one further spatial axis to mix the magnetic carriers.

9. A method for moving magnetic carriers in a controlled manner for performing immunoassays under weightlessness, comprising:
provided a sample volume in a vessel that includes magnetic carriers to perform an immunoassay under weightlessness in which no sedimentation and no convective heat transfer occurs in the sample volume;
providing permanent magnets on one spatial axis of the sample volume, the permanent magnets comprise several permanent magnets that are arranged as a matrix in which poles of the permanent magnets are arranged alternately;
moving the magnetic carriers within the sample volume by the permanent magnets slidably arranged relative to at least one spatial axis of the sample volume;
moving the permanent magnets in phase on the spatial axis of the sample volume to mix the magnetic carriers and the sample volume; and
shifting the permanent magnets into a parking position in which a screening device shields the permanent magnets from the sample volume when not used in a process step, wherein
for positioning of magnetic carriers on a plane within the sample volume, the permanent magnets are moved on a spatial axis that is perpendicular to the plane, wherein the permanent magnets lie, relative to the plane, diametrically opposite the magnetic carriers to be positioned, are in a first step moved in the direction of the sample volume and in a second step moved away from the sample volume.

* * * * *